United States Patent [19]

Ikeda et al.

[11] Patent Number: 4,904,793
[45] Date of Patent: Feb. 27, 1990

[54] TRIAZOLE COMPOUNDS, AND THEIR PRODUCTION

[75] Inventors: Takaharu Ikeda, Toyonaka; Kazuhiro Tada, Kyoto, both of Japan

[73] Assignee: Sumitomo Chemical Company, Limited, Osaka, Japan

[21] Appl. No.: 95,833

[22] Filed: Sep. 14, 1987

[30] Foreign Application Priority Data

Sep. 29, 1986 [JP] Japan .................................. 61-230481

[51] Int. Cl.⁴ .......................................... C07D 249/08
[52] U.S. Cl. .................................................... 548/262
[58] Field of Search ........................................ 548/262

[56] References Cited

U.S. PATENT DOCUMENTS

| 4,205,075 | 5/1980 | Baldwin et al. | 514/383 |
| 4,217,129 | 8/1980 | Shephard et al. | 548/262 |
| 4,246,020 | 1/1981 | Shephard et al. | 548/262 |

FOREIGN PATENT DOCUMENTS

| 53-18734 | 2/1978 | Japan | 514/383 |
| 57-140772 | 8/1982 | Japan | 548/262 |
| 57-140774 | 8/1982 | Japan | 548/262 |
| 57-142974 | 9/1982 | Japan | 548/262 |

OTHER PUBLICATIONS

Sumitomo IV, "Triazolyl Ketone Derivatives", CA 97:216197v (1982).

Primary Examiner—Glennon H. Hollrah
Assistant Examiner—Patricia L. Morris
Attorney, Agent, or Firm—Birch, Stewart, Kolasch & Birch

[57] ABSTRACT

A triazole compound of the formula:

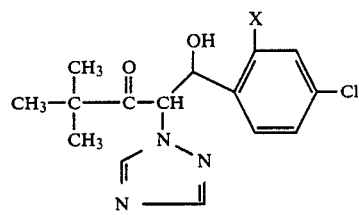

wherein X is a hydrogen atom or a chlorine atom, which can be produced by subjecting an aromatic aldehyde of the formula:

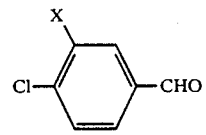

wherein X is as defined above, an alpha-halopinacolone of the formula:

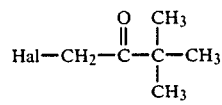

wherein Hal is a chlorine atom or a bromine atom and 1,2,4-triazole to condensation in the presence of an alkali, is useful as an intermediate in the synthesis of antimicrobial triazole-alcohols with high purity and high yield.

3 Claims, No Drawings

TRIAZOLE COMPOUNDS, AND THEIR PRODUCTION

This invention relates to triazole compounds, and their production. More particularly, the invention relates to novel triazole compounds useful as intermediates in the synthesis of anti-microbial agents, and their production.

The triazole compounds of the invention are representable by the formula:

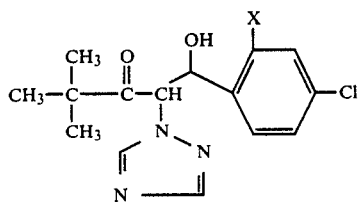

wherein X is a hydrogen atom or a chlorine atom, which cover specifically the following two compounds: 1-(4-chlorophenyl)-1-hydroxy-2-(1,2,4-triazol-1-yl)-4,4-dimethyl-1-pentan-3-one (I: X=H) and 1-(2,4-dichlorophenyl)-1-hydroxy-2-(1,2,4-triazol-1-yl)-4,4-dimethyl-1-pentan-3-one (I: X=Cl).

It is known that triazole-alcohols of the formula:

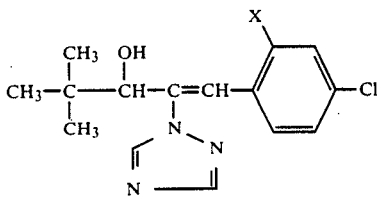

wherein X is as defined above are important anti-microbial agents (Japanese Patent Publication (unexamined) No. 41875/1979).

As described in this literature, the triazolealcohols (II) are produced by reacting 1-(1,2,4-triazol-1-yl)-3,3-dimethyl-2-butanone (hereinafter referred to as "triazolylpinacolone") with 2-chlorobenzaldehyde or 2,4-dichlorobenzaldehyde and reducing the resultant triazoleketone of the formula:

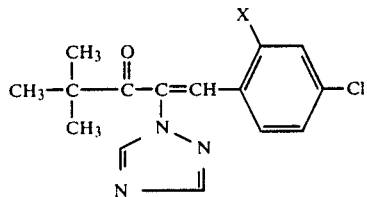

wherein X is as defined above. However, the starting triazolylpinacolone unlikely can be obtained in a pure state, and its purification requires an expensive distillation apparatus. When the triazolylpinacolone is used in a crude state, the triazole-ketone (III) and the triazole-alcohol (II) as produced are naturally crude. For purification of the triazole-ketone (III) or the triazole-alcohol (II), such an operation as crystallization is needed. However, purification through crystallization is economically disadvantageous, because depression in the yield of the triazolealcohol (II) as the objective product is produced by such operation.

As the result of an extensive study, it has been found that the triazole compounds (I) are readily obtainable in a highly pure state due to their easy crystallizability. Fortunately, the triazole compounds (I) can be dehydrated and reduced with ease to give the corresponding triazole-alcohols (II) with high purity and high yield. This invention is based on the above finding.

Accordingly, it is a main object of this invention to provide an improved process for production of the triazole-alcohols (II) with high purity and high yield. It is another object of the invention to provide the triazole compounds (I) useful as intermediates in such improved process.

In this connection, it may be noted that the triazole compounds (I) are disclosed generically in Japanese Patent Publication (unexamined) No. 18734/78 but not specifically. In fact, a process which can practically and successfully afford the triazole compounds (I) is not disclosed in this publication. In this sense, the triazole compounds (I) may be said to be novel.

According to the process of this invention, the triazole compound (I) is produced by subjecting an aromatic aldehyde of the formula:

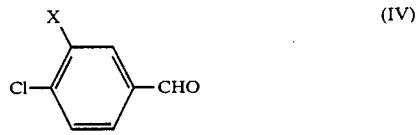

wherein X is as defined above, an alpha-halopinacolone of the formula:

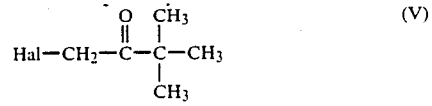

wherein Hal is a chlorine atom or a bromine atom and 1,2,4-triazole to condensation in the presence of an alkali.

Each of the three starting materials, i.e. the aromatic aldehyde (IV), the alpha-halopinacolone (V) and the 1,2,4-triazole, is not necessarily required to be highly pure and may have such a purity as indicated by ordinary industrial materials. As the aromatic aldehyde (IV), there may be used 4-chlorobenzaldehyde or 2,4-dichlorobenzaldehyde. As the alpha-halopinacolone (V), alpha-chloropinacolone or alpha-bromopinacolone may be used. The amounts of the aromatic aldehyde (IV) and of the 1,2,4-triazole to be used for condensation may be each usually from about 0.7 to 1.5 equivalents, preferably from about 0.8 to 1.2 equivalents, to the alpha-halopinacolone (V). Normally, the three starting materials are used in an equivalent ratio.

As to the kind of the alkali, any particular limitation is not present. Examples of the alkali are alkali metal hydroxides (e.g. sodium hydroxide), alkali metal carbonates (e.g. sodium carbonate, potassium carbonate), alkaline earth metal hydroxide (e.g. calcium hydroxide, barium hydroxide), alkaline earth metal carbonate (e.g. calcium carbonate), etc. These alkalis are usually employed in the form of aqueous solutions. The amount of the alkali to be used may be not less than about 0.5 mole, preferably from about 1 to 3 moles, to one mole of the alpha-halopinacolone.

The condensation can proceed in the absence of any solvent. For a smooth proceeding of the reaction and easy collection of the final product, however, the use of a solvent is preferred. As the solvent, there may be used any one inert to the reaction such as an aromatic hydrocarbon (e.g. benzene, toluene), a halogenated aromatic hydrocarbon (e.g. monochlorobenzene) or a halogenated aliphatic hydrocarbon (e.g. chloroform, dichloroethane). These may be used solely or in combination. When a non-polar solvent (e.g. benzene, monochlorobenzene) is used as the solvent, a phase transfer catalyst (e.g. tetra-n-butylammonium bromide) may be additionally incorporated therein so as to accelerate the reaction. The amount of the solvent may be optionally decided and is usually not less than about 0.3 parts by weight, preferably from about 0.5 to 10 parts by weight, to one part by weight of the combination of all the starting materials. The temperature of the reaction is usually from about $-10°$ to $100°$ C., preferably from about $0°$ to $50°$ C.

With the progress of the reaction, the objective triazole compound (I) is crystallized out. When desired, seed crystals may be added to the reaction system so that crystallization is promoted. When water is used in a small amount or not used as the solvent, by-produced inorganic salts may be separated out, but such inorganic salts can be readily eliminated by subsequent washing with water.

Recovery of the crystallized triazole compound (I) may be accomplished by per se conventional separation procedure such as filtration, centrifugation or decantation.

As explained above, the triazole compounds (I) are obtainable in high purity and high yield. Since the produced triazole compounds (I) are so highly pure, the triazole-alcohols (II) produced by their dehydration and reduction are also obtainable in high purity.

Practical and presently preferred embodiments of the invention are shown in the following Examples.

EXAMPLE 1

1,2,4-Triazole (69 g), alpha-bromopinacolone (162.2 g), 2.4-dichlorobenzaldehyde (121.5 g), tetra-n-butylammonium bromide (3 g) and monochlorobenzene (300 g) were charged in a flask and cooled to a temperature below 5° C. To the resultant mixture, a 50% aqueous solution of potassium hydroxide (108 g) was dropwise added at a temperature of 0° to 5° C. while stirring. After completion of the addition, stirring was further continued at 25 ° to 30° C. for 3 hours. The reaction mixture was filtered, and the collected powdery substance was washed with water and dried under reduced pressure to give 1-(2,4-dichlorophenyl)-1-hydroxy-2-(1,2,4-triazol-1-yl)-4,4-dimethyl-pentan-3-one (content, 97.6%; yield, 98.5%). m.p., 139°–141° C.

EXAMPLE 2

1,2,4-Triazole (6.9 g), alpha-bromopinacolone (179.1 g), tetra-n-butylammonium bromide (0.3 g) and 4-chlorobenzaldehyde (11.3 g) and monochlorobenzene (30 g) were charged in a flask and cooled to a temperature below 5° C. To the resultant mixture, a 50% aqueous solution of potassium hydroxide (10.8 g) was dropwise added at a temperature of 0° to 5° C. while stirring. After completion of the addition, stirring was further continued at the same temperature for 10 hours and at a temperature of 20° to 25° C. for 6 hours. The reaction mixture was filtered, and the collected powdery substance was washed with water and dried under reduced pressure to give 1-(4-chlorophenyl)-1-hydroxy-2(1,2,4-triazol-1-yl)-4,4-dimethyl-pentan-3-one (content, 97.4%; yield, 88.3%). m.p., 86°–87.5° C.

REFERENCE EXAMPLE 1

To 1-(2,4-dichlorophenyl)-1-hydroxy-2-(1,2,4-triazol-1-yl)-4,4-dimethyl-pentan-3-one (1,230 g; content, 98.0%) produced as in Example 1, monochlorobenzene (689 g) was added, and propionic acid (13.4 g) and piperidine (15.3 g) were added thereto. The resultant mixture was distilled at a temperature of 90° to 100° C. under reduced pressure for 8 hours to eliminate water azeotropically. The reaction mixture was cooled and washed with 20% sulfuric acid and water in order. The benzene layer was separated and concentrated to give 1-(2,4-dichlorophenyl)-2-(1,2,4-triazol-1-yl)-4,4-dimethyl-1-penten-3-one (1,089 g) (content, 93.7%; yield, 89.2%; E/Z ratio, 42.8/57.2).

To the above prepared 1-(2,4-dichlorophenyl)-2(1,2,4-triazol-1-yl)-4,4-dimethyl-1-penten-3-one (1,089 g), monochlorobenzene (3,687 g), bromine (15 g) and 98% sulfuric acid (315 g) were added, and the resultant mixture was stirred at 85° C. for 5 hours. The precipitated crystals were collected by filtration and washed with monochlorobenzene twice. To the thus washed crystals, monochlorobenzene (4,027 g) and water (735 g) were added, and the resulting mixture was stirred at 50° C. for 1 hour. The monochlorobenzene layer was separated and concentrated under reduced pressure to give the E isomer of 1-(2,4-dichlorophenyl)-2-(1,2,4-triazol-1-yl)-4,4-dimethyl-1-penten-3-one (991 g) (content, 98.4%; yield, 95.6%).

To d-norephedrine hydrochloride (832 g) and monochlorobenzene (2,343 g), a dimethylformamide solution of sodium borohydride (166 g) was added, and the resultant mixture was stirred at a temperature of 20° to 30° C. for 1 hour. A monochlorobenzene solution of the E isomer of 1-(2,4-dichlorophenyl)-2-(1,2,4-triazol-1-yl)-4,4-dimethyl1-penten-3-one (991 g) was added thereto, followed by stirring at the same temperature as above for 10 hours. The reaction mixture was treated with dilute nitric acid. The monochlorobenzene layer was separated and concentrated to give the E isomer of 1-(2,4-dichlorophenyl)-2-(1,2,4-triazol-1-yl)-4,4-dimethyl-1-penten-3-ol (1,000 g) (content, 97.0%; yield, 97.0%).

What is claimed is:

1. A triazole compound of the formula:

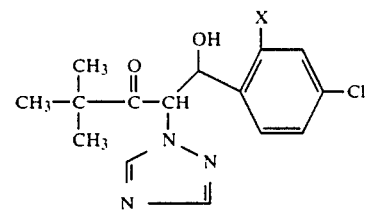

wherein X is a hydrogen atom or a chlorine atom.

2. The compound according to claim 1, which is 1-(4-chlorophenyl)-1-hydroxy-2(1,2,4-trizol-1-yl)-4,4-dimethyl-1-pentan-3-one.

3. The compound according to claim 1, which is 1-(2,4-dichlorophenyl)-1-hydroxy-2-(1,2,4-triazol-1-yl)-4,4-dimethyl-1-pentan-3 -one.

* * * * *